(12) United States Patent
Kroll

(10) Patent No.: US 6,804,557 B1
(45) Date of Patent: *Oct. 12, 2004

(54) BATTERY MONITORING SYSTEM FOR AN IMPLANTABLE MEDICAL DEVICE

(75) Inventor: Mark W Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 456 days.

This patent is subject to a terminal disclaimer.

(21) Appl. No.: 09/976,311

(22) Filed: Oct. 11, 2001

(51) Int. Cl.[7] .................................................. A61N 1/18
(52) U.S. Cl. ........................................................ 607/29
(58) Field of Search ...................................... 607/27–29

(56) References Cited

U.S. PATENT DOCUMENTS

| | | | |
|---|---|---|---|
| 4,681,823 A | 7/1987 | Tung et al. | 429/218 |
| 4,737,423 A | 4/1988 | Tung | 429/194 |
| 4,791,038 A | 12/1988 | Shia et al. | 429/218 |
| 4,809,697 A | 3/1989 | Causey, III et al. | 128/419 PT |
| 4,944,299 A | 7/1990 | Silvian | 128/419 PG |
| 5,114,810 A | 5/1992 | Frysz et al. | 429/194 |
| 5,466,254 A | 11/1995 | Helland | 607/123 |
| 5,836,973 A | 11/1998 | Kroll | 607/5 |
| 5,836,981 A | 11/1998 | Chang et al. | 607/9 |
| 6,108,579 A * | 8/2000 | Snell et al. | 607/29 |
| 6,275,734 B1 | 8/2001 | McClure et al. | 607/27 |
| 6,377,850 B1 * | 4/2002 | Takeuchi et al. | 607/2 |
| 6,671,552 B2 * | 12/2003 | Merritt et al. | 607/29 |

* cited by examiner

*Primary Examiner*—Mark Bockelman

(57) ABSTRACT

An implantable cardiac device, such as a pacemaker, provided with a carbon monofluoride ($CF_x$) battery. The $CF_x$ battery enables replacement of the typical voltage tripler with a voltage doubler and eliminates the need for a bulky decoupling capacitor. The device includes a precision A/D and voltage monitor to enable more accurate prediction of impending battery end-of-life. Several methods of accurately determining a pending end-of-life of a battery with a flat voltage output throughout discharge, such as a $CF_x$ battery, are provided.

36 Claims, 5 Drawing Sheets

BATTERY MONITORING SYSTEM FOR AN IMPLANTABLE MEDICAL DEVICE

FIELD OF THE INVENTION

The present invention relates to the field of implantable medical devices and, in particular, to a cardiac stimulation device employing a $CF_x$ battery for improved performance and a system for monitoring charge level of the battery.

BACKGROUND OF THE INVENTION

Implantable medical devices are typically battery powered devices that are implanted within the patient's body to have therapy available to the patient on a continuous basis. Battery failure is a particular problem with these devices as replacement of batteries often requires invasive surgical procedures. One particularly common type of implantable medical device is an implantable cardiac stimulation device.

Implantable cardiac stimulation devices, such as pacemakers and implantable cardioverter/defibrillators (ICD's), are employed to monitor cardiac activity and to provide therapy for patients with a variety of heart arrhythmias. Typically, these devices include sensors, that sense heart function and physiological parameters, and waveform generation and delivery systems, that provide electrical waveforms to the heart to correct arrhythmias and to ensure that more proper function of the heart is maintained. As the devices are implanted in a patient, it is desirable that the devices be as small and lightweight as possible in order to minimize impact on the patient.

Implantable cardiac stimulation devices are typically provided with batteries to power the monitoring and therapy delivery circuits. Due to the size constraints, the batteries used in implantable cardiac stimulation devices must be very small in size and yet able to provide power over a long period of time. Once the device is implanted, replacement of batteries typically involves invasive surgery. Hence, there is a strong desire to have small batteries that can provide significant power output to power the implantable device for extended periods of time. Known pacemaker devices typically use lithium iodine (LiI), commonly referred to as lithium batteries. Lithium batteries offer relatively high energy storage density and have known, predictable discharge characteristics.

While lithium batteries are commonly used for implantable cardiac stimulation devices, these batteries require additional circuitry that degrade device performance. Specifically, the performance characteristics of these batteries often require that additional circuitry be added to the device, thereby resulting in consumption of limited space in the implantable device and also consumption of limited power, or this additional circuitry has performance characteristics that limit the useful life of the implantable device.

For example, FIG. 1 illustrates a high-level conventional pacemaker circuit diagram of the prior art. Lithium batteries are typically not capable of providing pacing pulses at increased energy levels. As is shown in FIG. 1, a typical lithium battery and a decoupling capacitor are often connected in parallel to address this problem. The decoupling capacitor is used to accumulate electrical charge between pacing pulse events to enable the pacemaker to periodically deliver a pulse of energy at a greater rate than a lithium battery is capable of providing directly. The decoupling capacitor is continuously charged by the lithium battery and discharged upon a pacing event.

However, known implementations of the decoupling capacitors of the requisite electrical properties occupy a large fraction of the overall volume of the pacemaker device. As pacemakers shrink in size due to product refinement, the size of the capacitor is becoming an increasingly larger proportion of the total pacemaker volume and is presenting a limitation to further reduction in the size and weight of pacemaker devices.

FIG. 1 illustrates another aspect of known pacemaker designs, in particular, a voltage tripler that is part of the control circuitry for the pacemaker. The control circuitry performs the basic timing and monitoring functions of the device and delivers the pacing pulses to the patient's heart. The voltage tripler increases the voltage delivered by the lithium battery in order to provide a sufficient potential for effectively stimulating the heart. A lithium battery will have an open circuit voltage of approximately 2.7 VDC in a fully charged condition and approximately 2 VDC near the end of its life and thus requires a voltage tripler to generate the more than 5 VDC required for an effective pacing pulse. However, the voltage tripler is a source of overall system inefficiency as each voltage multiplication incurs some degree of loss.

A further drawback to the lithium battery will be apparent considering the output voltage characteristics illustrated in FIG. 2, which shows a typical voltage vs. charge delivery graph for typical lithium batteries. Multi-chamber pacing is a feature of many pacemaker systems and comprises supplying pacing stimuli to two different sites in the heart as opposed to pacing a single site. Typical parameters for a single-chamber pacing system with a lithium iodide battery at beginning of life would be an open circuit voltage of approximately 2.7 V (8.1 V after the voltage tripler) with an internal battery impedance of 300 Ω and a single lead of 500 Ω impedance. The voltage across the lead is regulated to be approximately 5 V and the pulsed current would be approximately 10 mA. Pulses are approximately 1 ms in duration and are applied every second, thus drawing a time averaged current of approximately 10 μA.

Similar multi-chamber pacing to two sites through two 500 Ω leads connected in parallel would draw a current pulse of approximately 20 mA and a time average current of 20 μA. However, as a lithium battery is discharged, the open circuit voltage drops while the internal resistance increases. After delivering approximately 900 mA-h, a typical lithium battery's output voltage decreases to approximately 2.4V and the internal impedance increases to approximately 10 kΩ. Under these parameters, delivering to two leads with 20 μA average current pulls the battery output voltage down to 2.2 V (2.4 V−20E-6 A×10E3 Ω) and thus approximately 6.6 V after the tripler. These battery conditions give marginal performance even with the voltage tripling.

With further use, i.e., further discharge of the lithium battery, the open circuit voltage continues to decrease and the ESR continues to increase to approximately 30 kΩ at EOL. Thus, while a lithium battery in this condition still has considerable charge remaining, the internal impedance and voltage at which the charge is available render a lithium battery unsuitable for continued multi-chamber pacing. Because of this factor, approximately 30–50% of the total typical lithium iodide battery's capacity is not usable and is wasted.

Thus, the typical lithium/lithium iodine battery currently in use in many implantable cardiac stimulation devices generally requires additional components to deliver the power needed to provide therapy and also has a limited life span in some implementations. Limited life span, of course, requires more periodic follow up and also requires more frequent replacement of the device. As stated above, more frequent replacement of the device is undesirable as it typically requires invasive surgical procedures.

A further difficulty that occurs with lithium/lithium iodine batteries in implantable medical devices is that the internal configuration of the battery often limits telemetry transfer rates. The power that the lithium battery provides is generally not sufficient to support data transfer rates from implantable cardiac stimulation devices that are in excess of approximately 8 Kbit of data. Typically, the decoupling capacitors are limited to only providing sufficient power to source the pacing pulses but do not have the capacity for providing sufficient charge to maintain voltage during a multi-minute, high speed transmission. This relatively low rate of data transfer therefore requires longer download periods to obtain data out of the implantable device which can be very inconvenient for the patient and the treating medical professional as well as consuming additional limited power from the battery.

Other battery technologies exist that may have application in implantable medical devices, however, these technologies have not generally been used due to implementation problems. One such technology is lithium-carbon monoflouride ($LiCF_{1.1}$), typically referred to as $CF_x$ batteries. $CF_x$ batteries have some desirable characteristics that show promise for use in implantable medical devices, such as pacemakers. Generally, $CF_x$ batteries have twice the mass energy density as lithium batteries and can thus provide significantly more electrical energy as lithium batteries of similar weight. Moreover, the performance characteristics are comparable to lithium based batteries.

However, the use of improved battery technologies, such as $CF_x$ batteries, in critical applications, such as implantable cardiac stimulation devices, has been limited by an inability to determine approaching end of life of the battery accurately and efficiently. In applications such as pacemakers and ICDs, it is imperative that the device be replaced prior to the battery failing. Battery failure will result in the device being unable to provide therapeutic simulation to the heart which can further result in catastrophic consequences for the patient.

$CF_x$ batteries provide a very stable voltage output throughout their effective life. As a consequence, $CF_x$ batteries do not exhibit output characteristics that are easily modeled to predict the end of life. Basically, these batteries generally maintain a substantially constant output voltage until the end of life and then their power output drops off very precipitously. This makes detection of approaching end of life of the battery extremely difficult. As a consequence, the application of $CF_x$ batteries to patient critical applications, such as pacemakers, ICDs and the like, has been extremely limited.

From the foregoing, it will be appreciated that there is a need for improved batteries for implantable medical devices such as pacemakers and ICDs. To this end, there is a need for a mechanism for detecting end of life of battery technologies, such as $CF_x$ batteries that have relatively constant output voltages over the length of their life to allow the use of these batteries in patient critical applications.

SUMMARY OF THE INVENTION

The aforementioned needs are satisfied by the implantable medical device of the present invention which, in one aspect, comprises an implantable medical device that is adapted to provide therapy to a patient that includes a battery that has a relatively constant output voltage until end of life and a voltage monitor that is monitoring the output voltage of the battery to thereby predict the end of life of the battery to enable the implantable medical device to signal the need of replacement of the battery.

In one particular implementation, the implantable medical device comprises an implantable cardiac stimulation device that includes a microcontroller and a battery, such as a $CF_x$ battery, that provides a constant output voltage, e.g., a variation of less than 200 millivolts over 1800 Milliampere hours of operation until end of life of the battery. At end of life of the battery, the supply voltage drops off rather precipitously, e.g., from approximately 2700 millivolts to 700 millivolts in less than 400 Milliampere hours.

The use of a voltage monitor permits the use of batteries, such as $CF_x$ type batteries, that have reduced internal resistance, also known as equivalent series resistance, thereby reducing the need for extra components such as de-coupling capacitors in pacemaker applications. Moreover, the reduced internal resistance also permits higher data transfer rates during telemetry and also reduces the need for voltage triplers as less energy of the battery is being absorbed by the battery itself.

In one particular implementation, the voltage monitor includes a band gap reference and a precise A/D, e.g., a 12 bit A/D that compares the battery voltage to the band gap reference voltage. This configuration is capable of monitoring the output voltage of the battery to within 1.0 millivolt resolution. The A/D provides a digital output signal to the microcontroller and the microcontroller evaluates the digital output signal to determine if the battery is approaching end of life. In one aspect, the microcontroller evaluates the signal to first determine a predicted end point of the battery and then evaluates the subsequent signals to determine if the output of the battery is approaching the predicted end point.

In one implementation, the microcontroller determines if the battery is approaching end of life by ascertaining a beginning of life voltage of the battery and then determines that end of life is approaching when the battery output voltage has fallen over time back to the beginning of life voltage. In another implementation, the microcontroller determines that end of life is approaching by periodically measuring the output voltage and determining when a peak output voltage has occurred. When measuring voltage, the voltage may vary slightly due to the current being drawn from the battery at any given time. To address this in one implementation, the battery voltage is periodically measured over a pre-selected period of time, e.g., once a day for a week, and a rolling average is maintained. The rolling average can be calculated daily such that the effect of periodic variations in the daily measurements are reduced. The end of life point of the battery is then predicted by determining when the output voltage of the battery has decreased a pre-selected quantity from the peak voltage. In yet another implementation, the end of life point of the battery is approximated by calculating a rate of consumption of the stored battery power and then determining a end of life point at the rate of consumption.

Each of the above-implementations can be used in conjunction with others to determine a correlated approaching end of life point for the battery. Once an end of life point is determined for the implantable medical device, the microcontroller of the implantable medical device can set a register indicating that the end of life has occurred or can otherwise enable an annunciator to advise the patient that it is time to seek replacement of the battery.

The use of such a monitoring system enables the use of improved batteries, such as $CF_x$ batteries in patient critical applications. The use of these types of batteries can result in more efficient power consumption, improved data transmission and the like. These and other objects and advantages of the present invention will be more apparent from the following description taken in conjunction with the accompanying drawings.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 3:
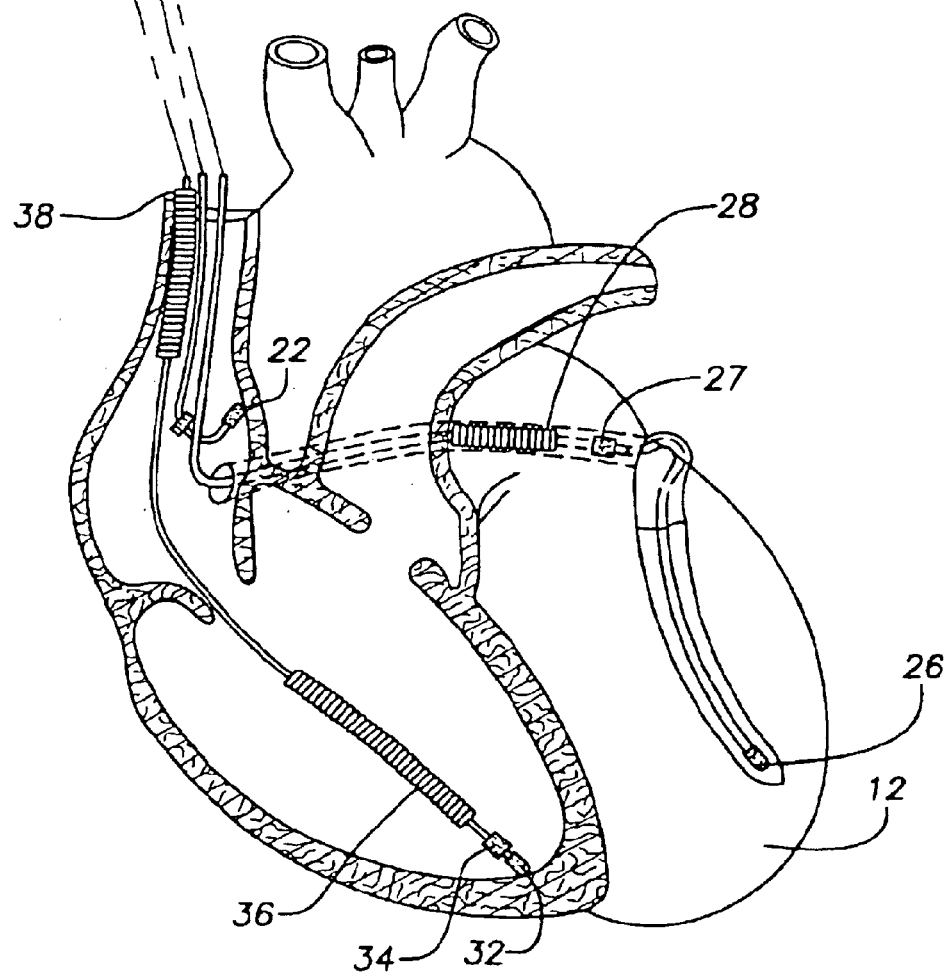
FIG. 3 is a simplified diagram illustrating an implantable stimulation device in electrical communication with at least three leads implanted into a patient's heart for delivering multi-chamber stimulation and shock therapy.

As shown in FIG. 3, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 091457,277, "A Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular Up electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 4:
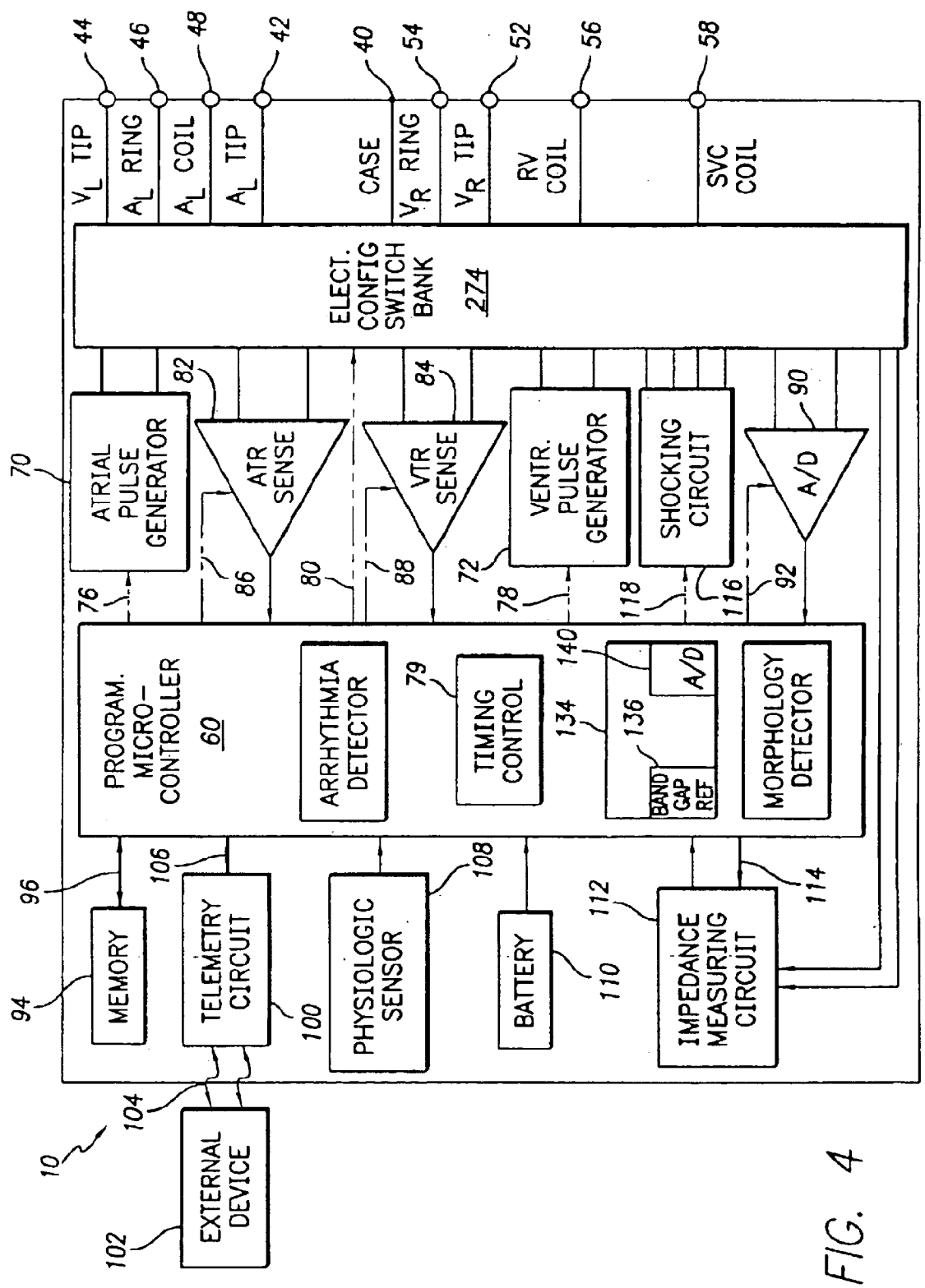
FIG. 4 is a functional block diagram of a multi-chamber implantable stimulation device illustrating the basic elements of a stimulation device which can provide cardioversion, defibrillation and pacing stimulation in four chambers of the heart.

As illustrated in FIG. 4, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 4, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and a superior vena cava (SVC) shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 4, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart 12, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart 12. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the simulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart 12.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a high-speed telemetry circuit 100 in telemetric communication with the external device 102, such as a programmer, transtelephonic transceiver, or a diagnostic system analyzer. The high-speed telemetry circuit 100 is activated by the microcontroller by a control signal 106. The high-speed telemetry circuit 100 advantageously allows intracardiac electrograms and status information relating to the operation of the device 10 (as contained in the microcontroller 60 or memory 94) to be sent to the external device 102 through an established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 091223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart 12, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device 10 additionally includes a battery 110 which acts as a primary power source to provide operating power to all of the circuits shown in FIG. 4. For the stimulation device 10, which employs shocking therapy, the battery 110 must be capable of operating at low current drains for long periods of time (preferably less than 10 $\mu$A) and then be capable of providing higher current pulses (for capacitor charging) when the patient requires a shock pulse (preferably, in excess of 100 mA, at voltages above 2 V, for periods of 100 seconds or more). The battery 110 must also have a predictable discharge characteristic so that elective replacement time can be detected. In this embodiment, the battery 110 is a carbon monofluoride ($CF_x$) battery. An example of a suitable $CF_x$ battery 110 is the model 9424 available from Wilson Greatbatch Ltd. of Clarence, N.Y.

Figure 2:
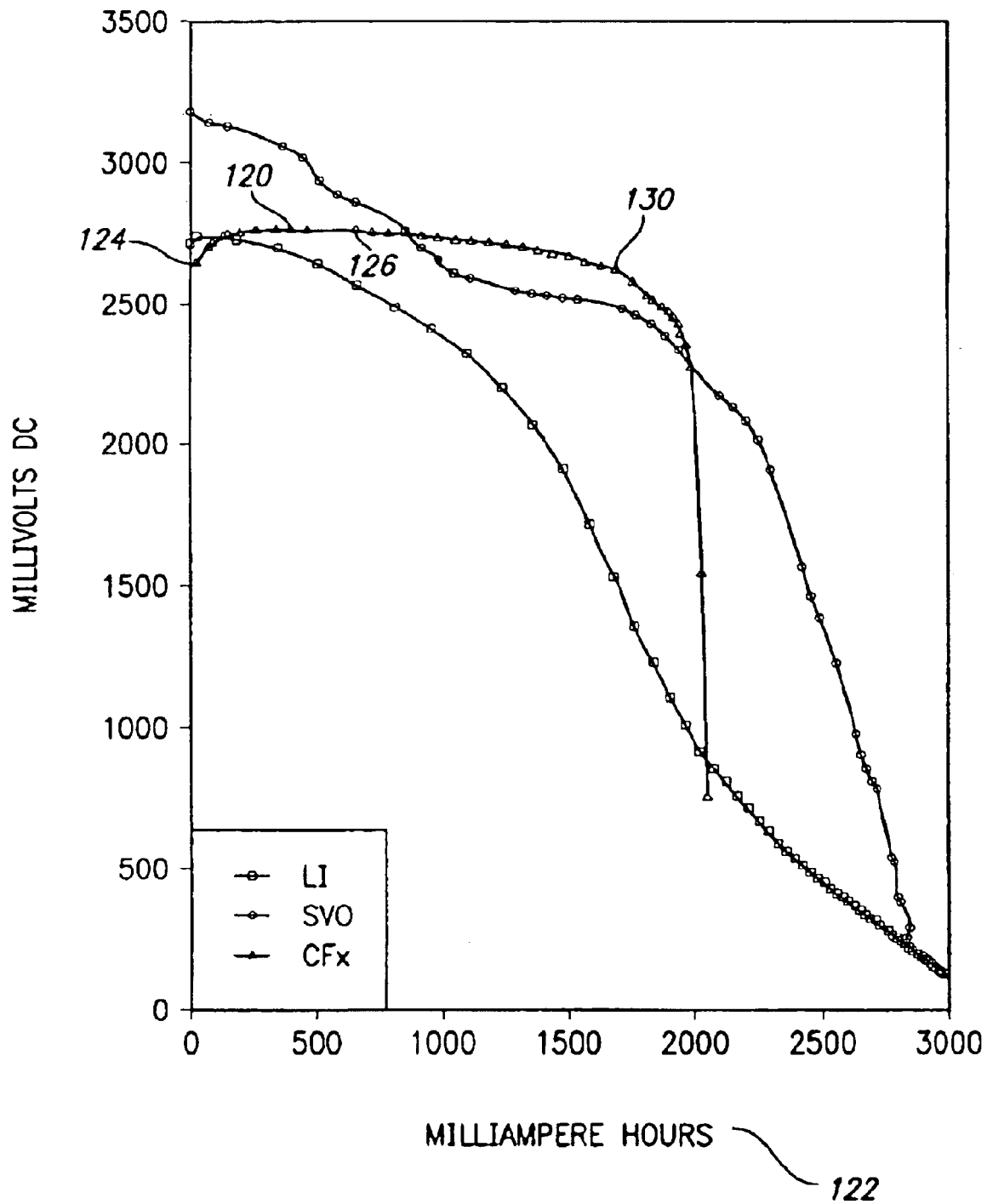
FIG. 2 is a graph of typical discharge characteristics of lithium, silver vanadium oxide, and $CF_x$ batteries.

The battery 110 preferably has an output voltage 120 that varies as the battery 110 delivers electrical charge 122 as illustrated in FIG. 2. The voltage 120 of the battery 110 has a beginning voltage 124, a peak voltage 126, and an end-of-life voltage 130. In this embodiment, the battery 110 has a beginning of life voltage that is approximately 2.4 volts and the output voltage 120 then rises to a peak voltage of approximately 2.72 volts after delivering approximately 600 milliampere-hours of charge 122. Subsequently, the output voltage decreases to a transition point, corresponding, in this implementation, to the end of life point 130, where the output voltage corresponds to the beginning of life voltage 124. It should be appreciated that the beginning voltage 124 and peak voltage 126 of the battery 110 of this embodiment are of different values and occur at different points of charge 122 delivery. Moreover, for any given battery, the magnitude of the beginning of life voltage, peak voltage, etc. can vary. However, for $CF_x$ batteries, the output voltage typically demonstrates the curve shown in FIG. 2.

In the implementation illustrated in FIG. 2, the $CF_x$ battery provides a particularly stable normal output voltage over a significant period of the battery's life, e.g., a variation of less than 150 millivolts DC over 1700 milliampere hours. As is generally illustrated, this particular battery provides an output voltage that is approximately 2.7 volts DC. The end of life point 130 is selected for the battery at a point where the battery 110 is transitioning between normal output and end of life where the output voltage begins to drop off significantly. As is illustrated in FIG. 2, the battery drops more than 1,900 millivolts in less than 400 milliampere hours. The relatively stable output voltage followed by the transition to a relatively sudden decrease in output voltage requires that additional monitoring be employed to ensure that the end of life point is detected.

The battery 110 of this embodiment is generally semicircular and approximately 45 mm×22 mm×5 mm. The battery 110 of this embodiment weighs approximately 7.6 g which is almost 7 g, or 47%, less than a comparable lithium-iodide battery. The battery 110 of this embodiment also has a beginning-of-life (BOL) equivalent series resistance (ESR) 132 of approximately 10 $\Omega$ and the battery's 110 ESR 132 increases to only approximately 1 k$\Omega$ near the battery's 110 end-of-life (EOL) 130. Thus, the battery 110 of this embodiment offers a substantially lower ESR 132 than the BOL ESR of approximately 300 $\Omega$ and EOL ESR of approximately 30 k$\Omega$ for a comparable lithium battery.

The lower ESR 132 of the battery 110 of this embodiment throughout its useful life provides an extended longevity of the device 10. In particular, the lower internal resistance of the battery 110 results in significantly less of the power of the battery 110 being dissipated as heat energy in the battery 110. Thus more battery power is available to be supplied to the component devices of the implantable medical device.

Specifically, with a standard lithium iodine battery as discussed above, the equivalent series resistance is typically so high that a de-coupling capacitor must be continuously charged in order to provide the needed power during pacing pulses. Since the equivalent series resistance of the $CF_x$ battery 110 is so much lower than the equivalent series resistance of the standard lithium iodine battery, the need for a de-coupling capacitor is reduced which thereby frees up more space for other components and can allow for more compact implantable devices.

Figure 1:
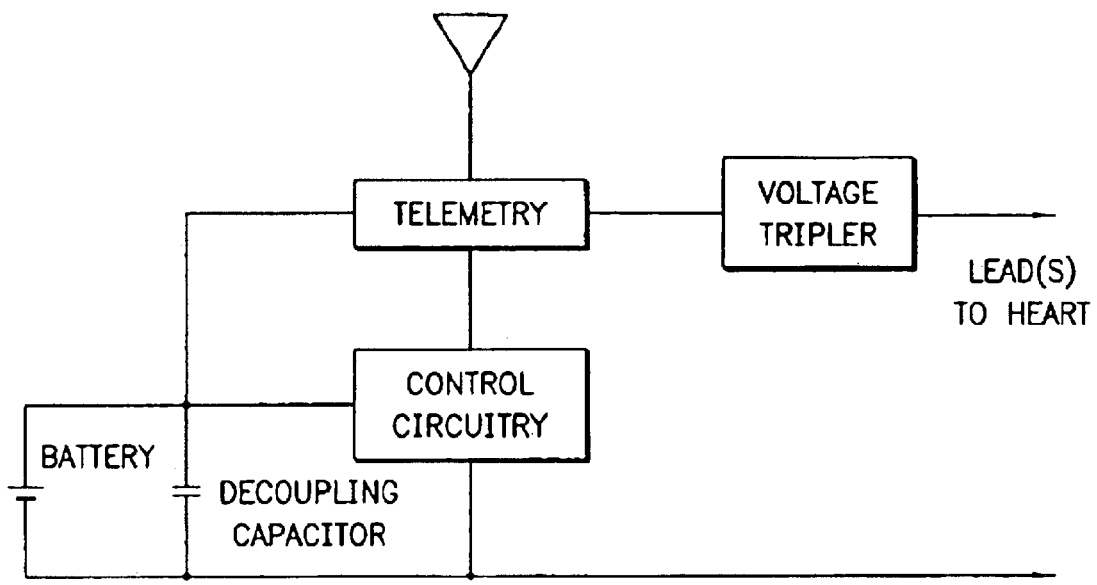
FIG. 1 is a high-level block circuit diagram of a typical prior art pacemaker employing a lithium battery.
Figure 5:
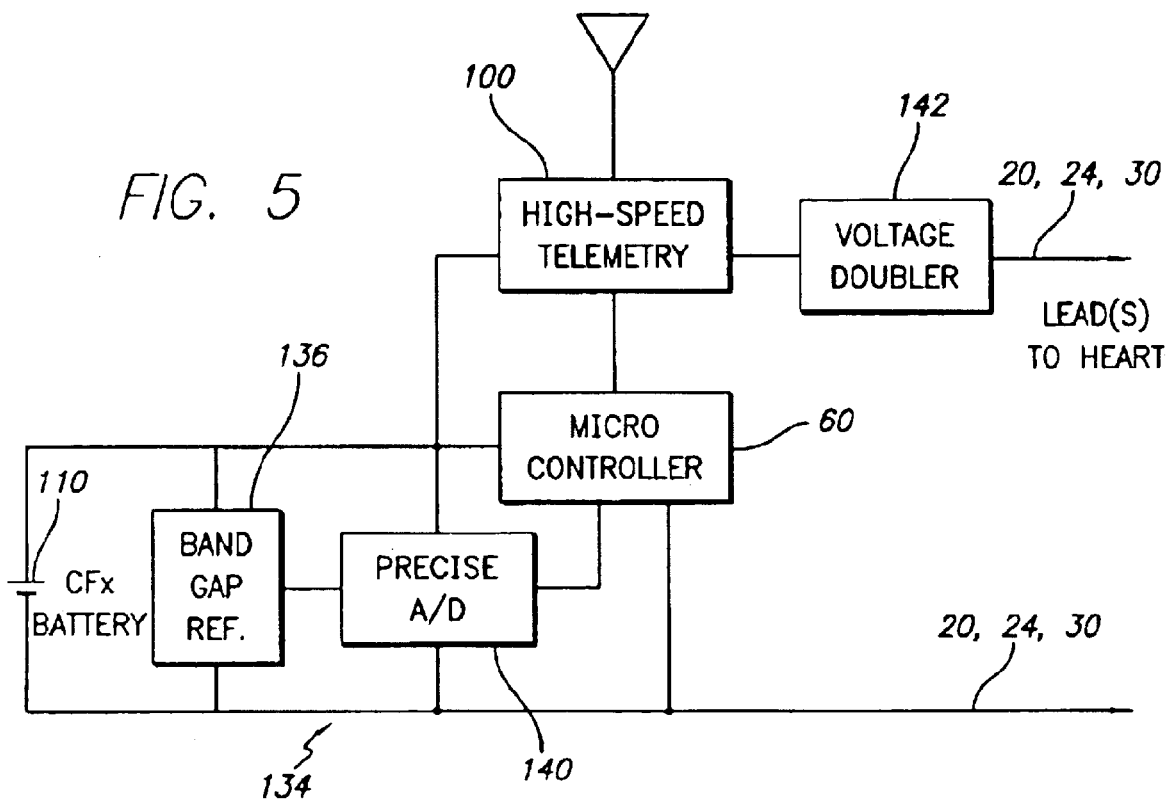
FIG. 5 is a block circuit diagram of a pacemaker provided with a $CF_x$ battery.

Moreover, the voltage and internal resistance characteristics of the battery 110 of this embodiment enable effective pacing with a voltage doubler 142 as illustrated in FIG. 5 as opposed to the voltage tripler of prior art pacers. The voltage doubler 142 doubles the voltage of signals provided to the voltage doubler 142 and is fabricated in a known manner. As discussed above, the lowered internal resistance of the battery 110 results in significantly less energy being dissipated as heat and thus allows for more current to be supplied to the leads 20, 24, 30. The use of a voltage doubler as opposed to a voltage tripler results in less dissipation of energy thereby prolonging battery life.

As discussed above in connection with FIG. 2, the end of life characteristics of the battery 110 are less easily predicted than prior art battery types. Specifically, a lithium iodine battery and an SVO type battery have a generally gradual decline in the output voltage versus milliampere hours. The gradual decline thus allows for greater predictability for when the battery is reaching end of life necessitating removal and replacement. However, as is illustrated in FIG. 2, the $CF_x$ battery 110 provides a substantially constant output voltage over a significant portion of its life and then it experiences a relatively sharp decline in the output voltage and the end of life. It is for this reason that $CF_x$ batteries have not been used in many implantable medical devices, the sudden end of life of the battery inhibits prior detecting of its imminent approach. To address this particular problem, the implantable medical device 10 incorporates a precision detector to detect voltages to predict and determine the approaching end of life of the battery to thereby allow the use of $CF_x$ batteries in more critical applications, such as implantable cardiac stimulation devices.

FIG. 5 is a schematic block diagram which illustrates the basic configuration of the battery monitoring circuit 134, the microcontroller 60, the telemetry 100 and the various components allowing for delivery of pacing pulses to the leads. As is indicated in FIG. 5, the $CF_x$ battery 110 is used to power a known band gap reference 136. As is understood, the typical band gap reference provides a very stable reference output that is both temperature and input voltage independent. Hence, variations in the output voltage developed by the battery 110 does not affect the output of the band gap reference 136 provided that the battery output is greater than a preselected minimum. In one implementation, the band gap reference 136 will provide an output voltage of 1.2 volts provided that the input voltage is greater than 1.5 volts. As is indicated in FIG. 2, the preferred $CF_x$ battery 110 will provide an output voltage on the order of approximately 2.6 to 2.7 volts until the end-of-life point is reached. As a consequence, the band gap reference 136 is capable of providing the 1.2 volt signal over the entire period of interest of the battery's life.

As is indicated in FIG. 5, the band gap reference 136 provides an output signal to a precise A/D converter 140. The precise A/D converter 140 is preferably a converter that has 12 bits of resolution and is, therefore, able to provide a digital signal to the programmable microcontroller 60 at a resolution of 1.0 millivolts or less. As is also indicated in FIG. 5, the precise A/D converter 140 also samples the output voltage of the battery 110 and it compares the output voltage of the battery 110 to the reference voltage provided by the band gap reference 136. Consequently, the precise A/D converter 140 is able to develop a digital word which is indicative of the difference between the output voltage of the battery 110 and the reference voltage provided by the band gap reference 136. This output voltage is then provided to the microcontroller 60 such that the microcontroller 60 thereby receives a signal indicative of the difference between the output voltage of the battery 110 and the reference voltage of the band gap reference 136.

As is described in greater detail below, the microcontroller 60 preferably receives this signal on a periodic basis, e.g., daily, such that the microcontroller 60 develops a history of the output voltage of the battery 110 that is very precise. By evaluation of this history of the output voltage, the microcontroller 60 can both predict an end of life point and then determine whether the predicted end-of-life point for the battery 110 is approaching.

As is be discussed in greater detail below, the end-of-life point can be determined using several different techniques without departing from the spirit of the present invention. In one particular implementation, the $CF_x$ battery 110 exhibits the output voltage characteristic as illustrated in FIG. 2. At initiation, or beginning of life, the battery 110 exhibits an initial beginning of life output voltage. The battery 110 then, over time, provides a somewhat increased output voltage until such time that the battery 110 is beginning to approach end of life. Consequently, in this implementation, the microcontroller 60 determines a predicted end of life as being the time period at which the voltage measured by the monitoring circuit 134 is equal to the originally measured beginning of life voltage.

In another implementation, the microcontroller 60 periodically receives the signal from the precise A/D converter 140 indicative of the battery 110 voltage and it then determines when a peak voltage has occurred. The microcontroller 60 then determines that the predicted end of life period occurs when the signal from the monitoring circuit 134 indicates that the output voltage has decreased a preselected amount from the peak voltage.

In yet another implementation, the microcontroller 60 includes a software routine that implements a fuel gauge. The output power provided by the battery 110 is either measured or modeled and, after a predetermined amount of power has been consumed, the microcontroller 60 then determines end of life has occurred. Naturally, any of the three preceding implementations can be correlated and used together to determine the end of life of the battery 110 without departing from the spirit of the invention.

In implementations where the voltage is measured, the measurement circuit 134 periodically provides a signal to the microcontroller 60, e.g., on a daily basis. The microcontroller 60 preferably processes the signal so as to determine a value indicative of the output voltage for the battery 110. The actual battery voltage measured on any given day may vary slightly due to events occurring at about the time the measurement is taken. For example, successive rapid discharges of the battery 110 immediately prior to taking the measurement may result in a temporarily lower reading.

The microcontroller 60 is preferably configured to take each of the individual measurements provided by the measurement circuit 134 and normalize it with respect to previous and/or subsequently obtained measurements. In one implementation, the microcontroller 60 uses a rolling average algorithm where each measurement is averaged together with a preselected number of previous and/or subsequent measurements to define a measurement value for a particular time period. Any number of different normalization techniques can be used to accommodate temporary variations in the measured output voltage of the battery 110 without departing from the spirit of the invention.

Figure 6:
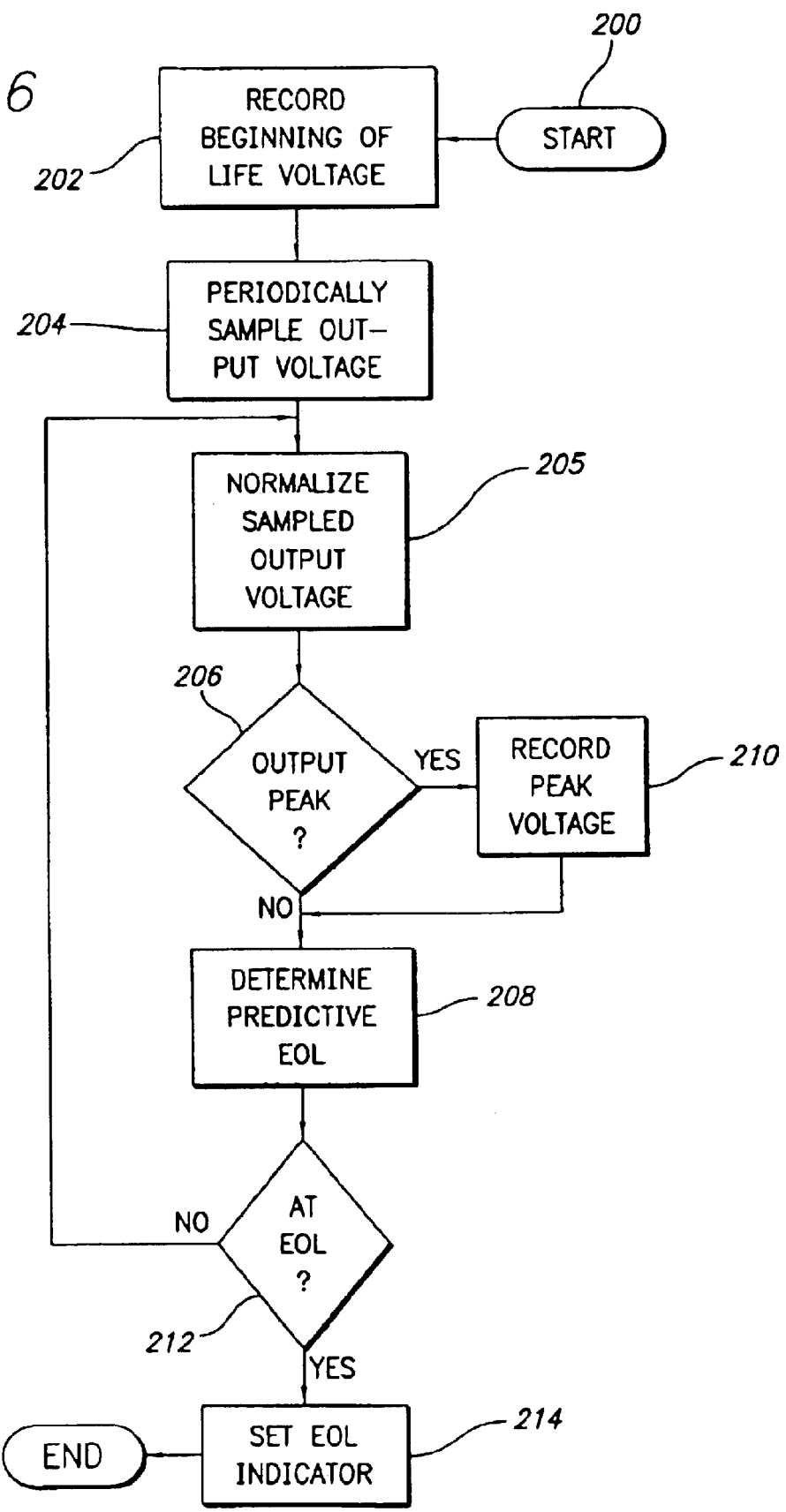
FIG. 6 is an exemplary flow chart illustrating the battery monitoring process implemented by the device of FIGS. 4 and 5.

FIG. 6 is a flow chart which illustrates one possible operation of the microcontroller 60 as it implements a first algorithm for determining the end of life point of the battery 110. This particular algorithm is simply exemplary and it can use either the beginning of life voltage or the peak voltage to determine a predictive end of life point of the battery 110. In particular, from a start state 200, the microcontroller 60 records the beginning of life voltage 202 upon power up of the implantable medical device 10.

Subsequently, the microcontroller 60 continues to periodically sample, in state 204, the output voltage provided by the A/D converter 240. The microcontroller 60 is preferably programmed so as to sample a signal indicative of the measured voltage at a periodic rate, e.g., every 12 hours or every 24 hours. The microcontroller 60 then preferably normalizes the sampled measurement in state 205. As discussed above, normalizing the sampled measurement reduces the impact of temporary variations in the battery 110 in the determination of end of life of the battery 110 and any of a number of normalization techniques can be used to obtain a normalized value including using the rolling averaging technique described above.

As is indicated in FIG. 6, the microcontroller 60 will also determine, in decision state 206, whether a peak voltage has been measured in state 204. The manner in which the microcontroller 60 determines whether a peak voltage has been determined can be done in any of a number of ways including evaluating a plurality of previously received normalized voltages for a peak followed by a subsequent decline in the normalized voltages. In one implementation, the end of life of the battery 110 is based upon a detected preselected decrease from the peak normalized voltage.

In another implementation, the time at which the peak normalized voltage has occurred can also be recorded by the microcontroller 60 such that this time component can provide a half-life indication of the remaining battery life on the assumption that the peak will occur at approximately half the usage of the battery 110. If the peak normalized voltage has been determined, the microcontroller 60 then records, in state 210, the peak normalized voltage and a time indication as to when it occurred. The microprocessor 60 then determines the predictive end of life point 130 of the battery 110. As described above in connection with FIG. 2, the predicted end of life point 130 preferably corresponds to the transition between the relatively constant normal output voltage of the battery 110 and the region of the battery curve where the battery 110 output voltage begins to decline precipitously.

The predicted end of life can either correspond to the time period at which the normalized sampled output voltage corresponds to the beginning of life voltage measured in state 202 or it can correspond to the time at which the normalized sampled output voltage has a magnitude that is a pre-selected amount less than the peak voltage. Hence, in this implementation, the microprocessor 60 is determining a voltage value that will occur in the future that is indicative of the battery 110 approaching an end of life condition. The microcontroller 60 continues to receive samples from the battery monitoring circuit 134 and it then can compare these values to the voltage value corresponding to the predicted end of life point of the battery 110.

Hence, the microcontroller 60 then determines, in decision state 212, whether the last measured normalized output voltage in state 204 is indicative of the end of life of the battery 110 in decision state 212. If it is not, the microcontroller 60 continues to sample the output voltage in state 204 as previously described until the end of life voltage is detected. As discussed above, several different implementations can be used to determine end of life of the battery 110.

Once the end of life point has been determined by the microcontroller 60 to have been met, the microcontroller 60 provides an indication of the approaching end of life such that upon subsequent monitoring of the implantable medical device 10 via the telemetry circuit 100, a treating medical professional will be advised by the microcontroller 60 that the end of life point of the battery 110 has been detected thereby allowing the treating medical professional to take appropriate action to replace the battery 110 or the implantable device 10. The microcontroller 60 can also be configured to initiate an annunciator to advise the patient that the end of life of the battery 110 is approaching to thereby induce the patient to seek assistance from a medical professional. These annunciators can either take the form of an audible tone or an electrical discharge that is sensed by the patient.

It will be further appreciated that, in some circumstance, it may be desirable to include other end of life detecting technologies in order to ensure that end of life of the battery 110 is accurately predicted and detected. For example, the use of a fuel gauge, which either measures or models the amount of power dissipated over time, can also be used by the implantable medical device 10 to determine approaching end of life. The fuel gauge routine can be a software implementation used by the microcontroller 60 to model or detect energy output so as to both provide a prediction as to when the end of life transition point will occur and whether the energy loss from the battery 110 is indicating that the end of life is approaching. This technique can be used in conjunction with the techniques described above in connection with FIG. 6 to improve the accuracy of both predicting when end of life will occur for a particular battery 110 and whether it has occurred.

From the foregoing it will be appreciated that the use of a sophisticated battery monitoring technique allows for the use of improved batteries such as a $CF_x$ battery 110 that has a precipitous end of life decline in battery voltage. The use of this type of battery 110 reduces the need for a decoupling capacitor in a pacemaker application and also allows for higher speed telemetry operation. Moreover, the significantly reduced internal resistance of the battery 110 further results in significantly less energy being consumed internally by the battery 110 which thereby results in more efficient use of the battery power and also does not require the use of voltage triplers in pacing applications.

Although the foregoing description of the preferred embodiment of the present invention has shown, described, and pointed out the fundamental novel features of the invention, it will be understood that various omissions, substitutions, and changes in the form of the detail of the apparatus as illustrated, as well as the uses thereof, may be made by those skilled in the art without departing from the spirit of the present invention. Consequently, the scope of the present invention should not be limited to the foregoing discussions, but should be defined by the appended claims.

What is claimed is:

1. An implantable medical device comprising:
   a therapy delivery device that is adapted to deliver therapy to an organ of a patient;
   a controller that controls the delivery of therapy to the organ of the patient;
   a battery that supplies power to the therapy delivery device, wherein the battery provides a substantially constant output voltage for a first period of time followed by a declining voltage as the battery approaches end of life;
   a battery monitoring circuit, that samples the output voltage of the battery and periodically provides sampled output voltage signals indicative thereof to the controller, wherein the controller determines a predicted end of life point of the battery based upon the sampled output voltage signals, and wherein the controller monitors the sampled output voltage signals and determines when at least one of the sampled voltage signals is indicative of the predicted end of life point of the battery.

2. The device of claim 1, wherein the battery is a $CF_x$ battery that has an output voltage characteristic that has an initial beginning of life voltage that increases to a peak voltage and then decreases to the predicted end of life point.

3. The device of claim 1, wherein the controller determines a beginning of life voltage value based on the sampled voltage output signals and uses the beginning of life voltage value to determine the predicted end of life point of the battery.

4. The device of claim 1, wherein the controller determines the predicted end of life point as the point at which the sampled output voltage signal has a magnitude corresponding to the magnitude of the beginning of life voltage value.

5. The device of claim 2, wherein the $CF_x$ battery has a beginning of life voltage of approximately 2.6 volts and a peak voltage of approximately 2.72 volts.

6. The device of claim 5, wherein the $CF_x$ battery provides an output voltage of between approximately 2.6 volts and 2.72 volts for approximately 1700 milliampere hours of operation.

7. The device of claim 1, wherein the controller determines a peak voltage value from the sampled output voltage signals and then determines a predicted end of life point of the battery as occurring when the sampled voltage signals have a magnitude that is a pre-selected magnitude less than the magnitude of the peak voltage value.

8. The device of claim 1, wherein the battery monitoring circuit comprises:

a band gap reference device coupled to the battery that provides a reference voltage that is substantially temperature independent and substantially voltage independent; and an A/D converter that receives the reference voltage and also receives the output voltage from the battery, wherein the A/D converter sends a digital signal to the controller indicative of the difference between the output voltage from the battery and the reference voltage.

9. The device of claim 8, wherein the A/D converter is a 12 bit A/D converter that provides a digital word to the controller that has a resolution of approximately 1 millivolt.

10. The device of claim 1, wherein the controller periodically receives a plurality of signals from the battery monitoring circuit and wherein the controller normalizes the periodically received values so as to reduce the effect of temporary variations in the output voltage of the battery.

11. The device of claim 10, wherein the controller averages each received sampled output voltage signal with a pre-selected number of previous sampled output voltage values to obtain a periodic value for evaluation of whether the periodic value is indicative of the predictive end of life of the battery.

12. The device of claim 1, wherein the battery monitoring circuit provides the sampled output voltage signals on a daily basis.

13. The device of claim 1, wherein the controller sets a flag to indicate that the end of life of the battery has been reached such that on subsequent review of the device by a treating medical professional, the treating medical professional is advised of the need to replace the battery in the implantable device.

14. The device of claim 1, wherein the therapy delivery device comprises at least one lead adapted to be implanted adjacent the heart of the patient so as to provide electrical stimulation to the heart.

15. The device of claim 1, wherein the controller senses the delivery of therapy by the therapy delivery device and further implements a fuel gauge routine that models battery energy output corresponding to the delivery of therapy and correlates the modeled battery energy output with the sampled voltage signals to determine whether the battery has reached the predicted end of life point.

16. An implantable cardiac stimulation device comprising:

at least one lead adapted to be implanted adjacent the heart so as to provide therapeutic stimulation to the heart;

a therapeutic stimulation circuit that develops electrical stimulation waveforms to be delivered via the at least one lead to the heart;

a controller that controls the delivery of therapeutic electrical stimulation to the heart of the patient;

a $CF_x$ battery that provides power to the implantable cardiac stimulation device wherein the battery has an output characteristic with a substantially constant output voltage for a first period of time followed by a declining voltage as the battery approaches end of life;

a battery monitoring circuit that samples the output voltage of the $CF_x$ battery and periodically provides sampled output voltage signals indicative thereof to the controller wherein the controller determines a predicted end of life point of the $CF_x$ battery based at least in part upon the sampled output voltage signals and wherein the controller monitors the sampled output voltage signals and determines when the sampled voltage signals are indicative of the predictive end of life point of the $CF_x$ battery.

17. The device of claim 16, wherein the implantable cardiac stimulation device comprises a pacemaker.

18. The device of claim 16, wherein the controller determines a predicted end of life point of the $CF_x$ battery at a point wherein the output voltage characteristic of the battery is transitioning between a substantially constant output and a declining voltage.

19. The device of claim 16, wherein the controller determines a beginning of life voltage value based on the sampled voltage output signals and uses the beginning of life voltage value to determine the predicted end of life point of the $CF_x$ battery.

20. The device of claim 19, wherein the controller determines the predicted end of life point as the point at which the sampled output voltage signals have a magnitude corresponding to the magnitude of the beginning of life voltage value.

21. The device of claim 20, wherein the $CF_x$ battery has a beginning of life voltage of approximately 2.6 volts and a peak voltage of approximately 2.72 volts.

22. The device of claim 21, wherein the $CF_x$ battery provides an output voltage of between approximately 2.6 volts and 2.72 volts for approximately 1700 milliampere hours of operation.

23. The device of claim 16, wherein the controller determines a peak voltage value from the sampled output voltage signals and then determines a predicted end of life point of the $CF_x$ battery as occurring when the sampled voltage signals have a magnitude that is a pre-selected magnitude less than the magnitude of the peak voltage value.

24. The device of claim 16, wherein the battery monitoring circuit comprises:

a band gap reference device coupled to the battery that provides a reference voltage that is substantially temperature independent and substantially voltage independent; and an A/D converter that receives the reference voltage and also receives the output voltage from the battery, wherein the A/D converter sends a digital signal to the controller indicative of the difference between the output voltage from the battery and the reference voltage.

25. The device of claim 24, wherein the A/D converter is a 12 bit A/D converter that provides a digital word to the controller that has a resolution of approximately 1 millivolt.

26. The device of claim 16, wherein the controller periodically receives a plurality of signals from the battery monitoring circuit and wherein the controller normalizes the periodically received values so as to reduce the effect of temporary variations in the output voltage of the $CF_x$ battery.

27. An implantable cardiac stimulation device comprising:

means for delivering therapy to the heart of a patient;

means for controlling the delivery of therapy to the heart of the patient;

means for supplying power to the implantable cardiac stimulation device wherein means for supplying provides a relatively constant output voltage over a normal useful life and then transitions into an end of life state wherein the output voltage declines from the relatively constant output voltage to a voltage that no longer supplies sufficient energy to enable the delivery of therapy to the heart of the patient;

means for monitoring the output characteristics of the battery, wherein the means for monitoring periodically samples an output characteristic of the means for supplying and provides an output signal indicative thereof, wherein the means for controlling receives the output signals and uses the output signals to (i) determine a predicted end of life point of the means for supplying whereby the means for supplying is approaching the point where it is transitioning between normal useful life into end of life and (ii) determining whether the output signals are indicative of the means for supplying having reached the predicted end point.

28. The device of claim 27, wherein the means for supplying comprises a $CF_x$ battery.

29. The device of claim 28 wherein the effective series resistance of the means for supplying at beginning of life and at the end of life is an order of magnitude less than the effective series resistance of an equivalent Li battery used in implantable cardiac stimulation devices.

30. The device of claim 27, wherein the means for delivering comprises a pacing lead.

31. The device of claim 27, wherein the means for delivering comprises an ICD coil.

32. The device of claim 27, wherein the means for monitoring comprises:

a band gap reference device coupled to the means for supplying that provides a reference voltage that is substantially temperature independent and substantially voltage independent; and an A/D converter that receives the reference voltage and also receives the output voltage from the means for supplying, wherein the A/D converter sends a digital signal to the means for controlling indicative of the difference between the output voltage from the means for supplying and the reference voltage.

33. The device of claim 27, wherein the means for controlling determines a predicted end of life point of the means for supplying by determining a beginning of life voltage for the means for supplying and determining that the predicted end of life point of the means for supplying will occur when the output signals from the means for monitoring indicate that the voltage of the means for supplying corresponds to the beginning of life voltage.

34. The device of claim 27, wherein the means for controlling determines a predicted end of life point of the means for supplying by determining a peak voltage of the means for supplying based on the output signals provided by the means for monitoring and then determining that the predicted end of life point of the means for supplying will occur when the output signals from the means for monitoring indicate that the voltage of the means for supplying has a magnitude that is a pre-selected amount less than the peak voltage.

35. The device of claim 27, wherein the means for controlling develops a normalized battery voltage signal corresponding to each of the output signals wherein the normalized battery voltage signal is processed so as to reduce the effect of temporary variations in the output voltage in the means for supplying.

36. The device of claim 35, wherein the means for controlling averages each receives sampled output signals with a pre-selected number of previous sampled output signals to obtain a periodic value for evaluation of whether the periodic value is indicative of the predicted end of life of the means for supplying.

* * * * *